United States Patent [19]

Farng et al.

[11] Patent Number: 4,828,733

[45] Date of Patent: May 9, 1989

[54] COPPER SALTS OF HINDERED PHENOLIC CARBOXYLATES AND LUBRICANTS AND FUELS CONTAINING SAME

[75] Inventors: Liehpao O. Farng; Horodysky Andrew G., both of Cherry Hill, N.J.

[73] Assignee: Mobil Oil Corporation, New York, N.Y.

[21] Appl. No.: 120,682

[22] Filed: Nov. 12, 1987

Related U.S. Application Data

[63] Continuation of Ser. No. 853,495, Apr. 18, 1986, abandoned.

[51] Int. Cl.[4] .......................................... C10M 129/50
[52] U.S. Cl. ..................................... 252/42.7; 44/68; 252/400.1; 524/328; 524/582; 556/113; 556/114; 556/115
[58] Field of Search ................ 252/42.7, 400.1; 44/68; 556/114, 115, 113; 524/328, 582

[56] References Cited

U.S. PATENT DOCUMENTS

| | | | |
|---|---|---|---|
| 2,252,662 | 8/1941 | Reiff | 252/400.1 |
| 2,417,087 | 3/1947 | Prutton | 252/42.7 |
| 2,677,659 | 5/1954 | Reiff | 252/42.7 |
| 2,903,487 | 9/1959 | Coffield | 44/68 |
| 3,310,575 | 3/1967 | Spivack | 44/68 |
| 3,594,318 | 7/1971 | O'Neill | 44/68 |
| 3,723,489 | 3/1973 | Dexter | 556/114 |
| 4,225,448 | 9/1980 | Braid | 252/42.7 |

*Primary Examiner*—William R. Dixon, Jr.
*Assistant Examiner*—Margaret B. Medley
*Attorney, Agent, or Firm*—Alexander J. McKillop; Charles J. Speciale; Van D. Harrison, Jr.

[57] ABSTRACT

Copper salts of hindered phenol carboxylic acids are used in lubricants and fuels compositions as an antioxidant.

10 Claims, No Drawings

COPPER SALTS OF HINDERED PHENOLIC CARBOXYLATES AND LUBRICANTS AND FUELS CONTAINING SAME

This is a continuation of copending application Ser. No. 853,495, filed on Apr. 18, 1986.

NATURE OF INVENTION

This invention is concerned with a novel group of copper salts of hindered phenolic carboxylates and their use in liquid hydrocarbon fuels and lubricants as friction reducing, fuel economy, antioxidant and wear protection additives.

SUMMARY OF THE INVENTION

In accordance with this invention there is provided a reaction product which constitutes primarily the copper salts of hindered phenol carboxylic acids. The invention also provides lubricant and fuel compositions comprising a major proportion of lubricant or fuel and a minor, antifriction, fuel comsumption reduction, or antioxidant amount of the copper compound.

DETAILED DESCRIPTION OF THE INVENTION

The hindered phenol carboxylic acids useful in this invention generally have the formula

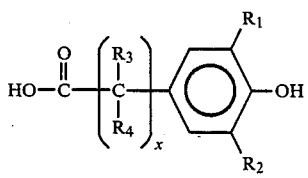

where $R_1$ or $R_2$ = hydrogen, or hydrocarbyl groups containing 1 to 18 carbon atoms, or tertiary alkyl or aralkyl groups containing 4 to 8 carbon atoms (but both $R_1$ and $R_2$ cannot be hydrogen) $R_3$ or $R_4$ = hydrogen, or hydrocarbyl groups, or aralkyl groups, or cycloalkyl groups, x=0 to 24. Particularly preferred sources of this acid are substituted derivatives of benzoic acid such as 3,5di-tert-butyl-4-hydroxy benzoic acid, etc.

The source of copper ions can be any copper salt. Preferred copper salts include cupric acetate hydrate ($Cu(C_2H_3O_2)_2 \cdot H_2O$), basic cupric acetate ($Cu(C_2H_3O_2)_2 \cdot CuO \cdot 6H_2O$), cuprous carbonate ($Cu_2CO_3$), basic cupric carbonate ($CuCO_3 \cdot Cu(OH)_2$), cuprous hydroxide (CuOH) and cupric hydroxide ($Cu(OH)_2$), and other similar copper compounds.

The hindered phenol carboxylic acids are reacted with the copper salts in almost molar quantities or less or more than molar quantities to make neutral, acidic, or basic salts. The reaction is thought to go as follows:

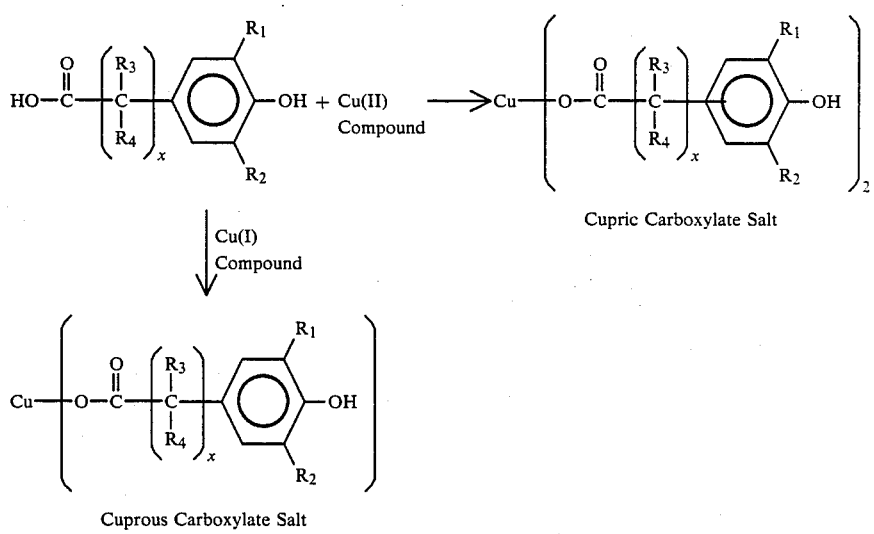

where all the R groups, and x have the definitions provided above.

The copper salts generally are made by either of two processes:

In the "fusion process" a metallic oxide, hydroxide or salt of a weak acid is reacted directly with a selected carboxylic acid at an elevated temperature.

As water is driven off (an inert solvent such as toluene, or xylene can be employed as a carrier to drive out water or weak acid azeotropically) the reaction is completed to form a molten mass which is cooled, crushed, pulverized, and classified for desired particle size.

The "precipitation process" involves preparation of a dilute, soluble carboxylate solution (sodium or potassium carboxylate) or carboxylic acid solution (appropriate reaction media are water, alcohol, etc.). A separately prepared solution of an inorganic salt of the desired metal is then added to the soluble carboxylate solution or carboxylic acid solution to bring about precipitation of the metal-organic product. Normally, the reaction is conducted primarily at or near room temperature.

The hydrocarbon compositions hereof may comprise any oleaginous materials utilized under conditions that require lubricative properties under extreme pressure conditions and require protection against excessive wear under operating conditions, and/or normally exhibit insufficient anti-corrosion properties. Especially suitable for use with the additives of this invention are liquid hydrocarbon oils of lubricating viscosity. Lubricant oils, improved in accordance with the present invention, may be of any suitable lubricating viscosity. In general, the lubricant compositions may comprise any mineral or synthetic oil of lubricating viscosity or mixtures thereof. The additives of this invention are especially useful in greases and in automotive fluids such as brake fluids and power brake fluids, transmission fluids, power steering fluids, various hydraulic fluids and gear oils and in liquid hydrocarbyl fuels.

In instances where synthetic oils are desired in preference to refined petroleum or mineral oil they may be employed alone or in combination with a mineral oil. They may also be used as the vehicle or base of grease compositions. Typical synthetic lubricants include polyisobutylene, polybutenes, hydrogenated polydecenes, polypropylene glycol, polyethylene glycol, trimethylol propane esters, neopentyl and pentaerythritol esters of carboxylic acids, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis(p-phenoxy phenyl) ether, phenoxy phenylethers, dialkylbenzenes, etc.

As hereinbefore indicated, the aforementioned additives can be incorporated as additives in grease compositions. When high temperature stability is not a requirement of the finished grease, mineral oils having a viscosity of at least 40 SSU at 150° F. are useful. Otherwise those falling within the range of from about 60 SSU to about 6,000 SSU at 100° F. may be employed. The lubricating compositions of the improved greases of the present invention, containing the above-described additives, are combined with a grease forming quantity of a thickening agent. For this purpose, a wide variety of materials can be dispersed in the lubricating oil in grease-forming qualities in such degree as to impart to the resulting grease composition the desired consistency. Exemplary of the thickening agents that may be employed in the grease formulation are metal soaps as well as non-soap thickeners, such as surface-modified clays and silicas, aryl ureas, calcium complexes and similar materials. In general, grease thickeners are employed which do not melt or dissolve when used at the required temperature within a particular environment; however, in all other respects, any material which is normally employed for thickening or gelling oleaginous fluids or forming greases may be used in the present invention.

Generally the lubricants and fuels of the present invention contain an amount of the copper compound effective to improve extreme pressure properties and antiwear and oxidation characteristics. Normally this amount will be about 0.0005 to 5%, preferably about 0.005 to 0.5%, of the total weight of the lubricant composition.

Other additives may be present for their known purposes in combination with the sulfurized olefinic product of the present invention. Such additives include, for example, detergents and dispersants of the ash-producing or ashless type, corrosion-inhibiting agents, auxiliary oxidation-inhibiting agents, pour point depression agents, auxiliary extreme pressure agents, color stabilizers and anti-foam agents.

We have further discovered that the reaction product of this invention when mixed with state of the art antioxidants such as phenolic and arylamine antioxidants further effects an unexpected increase in the effectiveness of those antioxidants. The aryl amine antioxidants can include alkylated aryl amines, oxidized aryl amines, diaryl amines, alkylated diaryl amines as well as quinoline, phenyl-alpha-naphthyl amine, coupled aryl or diarylamines and the like, naphthyl amines, diphenyl amine derivatives, para-phenylenediamines, quinolines and hydroquinolines. Phenolics can include hindered phenols, such as di-tertiary-butyl, para cresol, di-tertiary-butyl phenol and the phenolics of Table I and sulfur-containing phenols. Also included are monophenols, bisphenols, thiobisphenols, polyphenols and hydroquinone derivatives. In utilizing a mixture of state of the art antioxidants with the hindered phenolic carboxylates of this invention, it is preferred that the ratio of additional antioxidant to hindered phenolic carboxylate antioxidants in the mixture be between 1 and 1000 moles per mole or pounds per pound. The concentration of the mixture in the liquid hydrocarbon lubricant or fuel will be at least about the same as up to hundredth more times than that for the hindered phenolic carboxylate when used alone.

Example 1

Cupric (3,5di-tert-butyl-4-hydroxy) benzoate was prepared by metathesis of alcoholic copper (II) acetate with an alcoholic solution of the appropriate acid as follows: A quantity, 25.0 grams of 3,5-di-tert-butyl-4-hydroxybenzoic acid and 300 ml. of absolute methanol were placed in a 1000 ml. Erlenmyer flask with agitation. Slowly, ten grams of cupric acetate monohydrate $(Cu(C_2H_3O_2)_2 \cdot H_2O)$ in 500 ml. of methanol were added to the stirred reactants and the entire, homogeneous solution was mixed at 40°–45° C. over the course of five hours, and then at room temperature for an additional sixteen hours. The resulting precipitate was filtered off and washed with water, until free from excess precipitant, and with a little alcohol to remove free acids. The precipitant was then oven dried to obtain the desired salts (27.8 grams). The product was characterized by the disappearance of hydroxyl group, and the appearance of carboxylate infrared absorption at 1400 cm$^{-1}$ and 1800 cm$^{-1}$. The product had a royal blue color and contained 10.8% of copper.

The product was blended into fully formulated oils and tested in a catalytic oxidation test for lubricants. The test lubricant composition was subjected to a stream of air which was bubbled through the composition at a rate of 5 liters per hour at 325° F. for 40 hours. Present in the composition were metals commonly used as materials of engine construction, namely:

(a) 15.6 sq. in. of sand-blasted iron wire.
(b) 0.78 sq. in. of polished copper wire.
(c) 0.87 sq. in. of polished aluminum wire, and
(d) 0.167 sq. in. of polished lead surface.

Inhibitors for oil are rated on the basis of prevention of oil deterioration as measured by the increase in acid formation or neutralization number($\Delta$NN) and kinematic viscosity ($\Delta$KV) occasioned by the oxidation. Compounds in accordance with this invention tested for their oxidative stabilizing properties in accordance with the above Catalytic Oxidative Test proved highly effective oxidation stabilizers and/or inhibitors.

In assessing the results of this test, it will be understood that the more important consideration is the control of viscosity increase ($\Delta$KV). Results are shown in Table 1 & 2. A comparison of the oxidation-inhibiting characteristics of this product with the other hindered phenols in fully formulated oils is included in Table 1.

TABLE 1

| | Antioxidant Evaluation | | | |
|---|---|---|---|---|
| | Additive Conc. (Wt. %) | Sludge Rating | Change in Acid Value | % Change in Viscosity |
| Base Oil A (150 second, fully formulated, solvent refined paraffinic bright oil containing defoamant/demulsifier/antiwear/anticorrosion/EP/antirust performance package). | — | Nil | 2.58 | 30.61 |
| Cupric (3,5-di-tert-butyl-4-hydroxy) benzoate (Example 1) | 0.01 | Nil | 1.49 | 25.62 |
| 2,6-di-tert-butylphenol | 0.01 | Trace | 1.23 | 32.67 |
| | 0.10 | Trace | 1.67 | 31.34 |
| | 0.50 | Mod. | 1.34 | 30.70 |
| 2,6-di-tert-butyl-p-cresol | 0.01 | Trace | 1.89 | 32.15 |
| | 0.10 | Trace | 2.16 | 29.59 |
| 4,4-methylenebis(2,6-di-tert-butylphenol) | 0.10 | Light | 1.11 | 27.26 |
| 4,4-thiobis(2-tert-butyl 6-methylphenol) | 0.01 | Trace | 1.18 | 29.63 |
| | 0.10 | Mod. | 0.88 | 26.09 |

As little as 0.01% in a fully formulated mineral oil based gear oil of the product of Example 1 controls the increase in viscosity of the test oil much better than equal or greater concentrations of more traditional hindered phenolic antioxidants as shown in Table 1. In fact, even ten times the concentration of alternate hindered phenols are not as effective as Example 1 in controlling viscosity increase due to oxidation.

TABLE 2

| | Antioxidant Evaluation | | | |
|---|---|---|---|---|
| | Additive Conc. (Wt. %) | Sludge Rating | Change in Acid Value | % Change in Viscosity |
| Base Oil B (fully formulated synthetic gear oil containing antiwear/anticorrosion/EP/antirust performance package. | — | Light | 4.90 | 25.2 |
| Cupric (3,5-di-tert-butyl-4-hydroxy) benzoate (Example 1) | 0.05 | Nil | 2.28 | 21.4 |
| | 0.10 | Nil | 1.62 | 5.1 |
| | 0.20 | Light | −0.18 | −2.06 |
| | 0.50 | Light | 0.15 | 5.27 |

As demonstrated above, these novel antioxidants show remarkable activity in synthetic oil formulations.

As noted previously, the compositions of this invention when mixed with state-of-the-art antioxidants effectively enhances their ability to reduce oxidation. These synergistic mixtures work better than equivalent concentrations of the individual components. This is demonstrated in Table 3 below with two types of known antioxidants, phenolic and aryl amine. In these tests the product from Example 1 was mixed and tested as shown.

TABLE 3

| | Antioxidant Evaluation | | | |
|---|---|---|---|---|
| | Additive Conc. (Wt. %) | Sludge Rating | Change in Acid Value | % Change in Viscosity |
| Base Oil A (fully formulated mineral oil) | — | Nil | 2.58 | 30.61 |
| Cupric (3,5-di-tert-butyl-4-hydroxy) benzoate (Example 1) | 0.01 | Nil | 1.49 | 25.62 |
| Phenolic antioxidant-Irganox L-130 | 0.50 | Nil | 2.22 | 27.16 |
| Arylamine antioxidant-Irganox L-57 | 1.00 | Light | 1.93 | 29.74 |
| Cupric (3,5-di-t-butyl-4-hydroxy) benzoate (Example 1) | 0.01 | Nil | −0.39 | −2.62 |
| Phenolic antioxidant-Irganox L-130 | 0.50 | | | |
| Cupric (3,5-di-t-butyl-4-hydroxy) benzoate (Example 1) | 0.01 | Nil | −0.31 | 3.49 |
| Arylamine antioxidant-Irganox L-57 | 1.00 | | | |

The Irganox antioxidant of Table 3 is a commercial product marketed by Ciba-Geigy Inc.

The product of Example 1 also shows some strong synergistic effects with the presence of other antioxidants as shown in Table 3. Synergistic antioxidant activity is demonstrated with the use of Example 1 along with (a) phenolic antioxidants and (b) arylamine antioxidants.

We claim:
1. A lubricating oil or grease composition comprising
(a) a liquid hydrocarbon and between about 0.0005 and about 5 percent by weight of the total composition of
(b) a copper salt of a hindered phenolic substituted carboxylic acid, said copper salt having the structural formula:

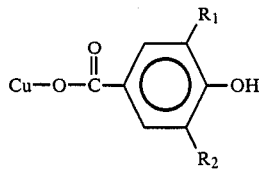

where $R_1$ or $R_2$ = hydrogen, or hydrocarbyl groups containing 1 to 8 carbon atoms, or tertiary alkyl or aralkyl groups containing 4 to 8 carbon atoms both $R_1$, and $R_2$ not being a hydrogen atom simultaneously.

2. The composition of claim 1 wherein said copper salt is present in a concentration of 0.01%.

3. The composition of claim 1 wherein said acid is benzoic acid.

4. A hydrocarbon composition comprising
(a) a lubricating oil or grease and between about 0.0005 and about 5 percent by weight of the total composition of
(b) a copper salt of a hindered phenolic substituted carboxylic acid, said copper salt having the structural formula:

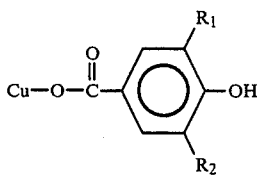

where $R_1$ or $R_2$ = hydrogen, or hydrocarbyl groups containing 1 to 8 carbon atoms, or tertiary alkyl or aralkyl groups containing 4 to 8 carbon atoms both $R_1$ and $R_2$ not being a hydrogen atom simultaneously.
(c) an antioxidant selected from the group consisting of aryl amines, alkylated aryl amines, oxidized aryl amines, diaryl amines, alkylated diaryl amines, naphthyl amines, diphenyl amine derivatives, para-phenylenediamines, quinoline, hydroquinoline, phenyl-alpha-naphthyl amine and coupled aryl or diarylamine, the ratio of antioxidant to copper salt being between about 1 and about 1000 parts by weight of antioxidant to 1 part of copper salt.

5. A method of treating a hydrocarbon liquid comprising adding to it between about 0.0005 and about 5 percent by weight of the total composition of an antioxidant and a copper salt of a hindered phenolic substituted carboxylic acid, said copper salt having the structural formula:

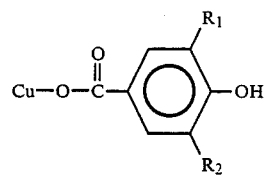

where $R_1$ or $R_2$ = hydrogen, or hydrocarbyl groups containing 1 to 8 carbon atoms, or tertiary alkyl or aralkyl groups containing 4 to 8 carbon atoms both $R_1$ and $R_2$ not being a hydrogen atom simultaneously, the ratio of antioxidant to copper salt being between about 1 and about 1000 parts by weight of antioxidant to 1 part of copper salt.

6. The method of claim 5 wherein said antioxidant is a phenol.

7. The method of claim 5 wherein said antioxidant is an arylamine.

8. The method of claim 5 wherein said antioxidant is selected from the group consisting of aryl amines, alkylated aryl amines, oxidized aryl amines, diaryl amines, alkylated diaryl amines, naphthyl amines, diphenyl amine derivatives, para-phenylenediamines, quinoline, hydroquinoline, phenyl-alpha-naphthyl amine and coupled aryl or diarylamine.

9. The method of claim 6 wherein the phenol is selected from the group consisting of hindered phenols, sulfur containing phenols, monophenols, bisphenols, thiobis phenols, polyphenols and hydroquinone derivatives.

10. The method of claim 6 wherein the phenol is selected from the group consisting of 2,6-di-tertiarybutyl para cresol, 2,6-tertiary butyl phenol, 4,4-methylene-bis (2,6di-tert-butyl phenol) and 4,4-thiobis(2-tert-butyl 6-methylphenol).

* * * * *